United States Patent
DuBourdieu et al.

(10) Patent No.: US 12,390,513 B2
(45) Date of Patent: Aug. 19, 2025

(54) COMPOSITIONS AND METHODS FOR TREATING PANCREATIC ENZYME DEFICIENCIES IN MAMMALS

(71) Applicant: Vets Plus, Inc., Menomonie, WI (US)

(72) Inventors: Daniel J. DuBourdieu, Limerick, ME (US); Jamil Talukder, Menomonie, WI (US); Rajiv Lall, Menomonie, WI (US)

(73) Assignee: Vets Plus, Inc., Menomonie, WI (US)

( * ) Notice: Subject to any disclaimer, the term of this patent is extended or adjusted under 35 U.S.C. 154(b) by 225 days.

(21) Appl. No.: 18/071,857

(22) Filed: Nov. 30, 2022

(65) Prior Publication Data

US 2023/0118104 A1   Apr. 20, 2023

Related U.S. Application Data

(63) Continuation of application No. 16/549,705, filed on Aug. 23, 2019, now Pat. No. 11,547,745.

(60) Provisional application No. 62/721,677, filed on Aug. 23, 2018.

(51) Int. Cl.
| | | |
|---|---|---|
| *A61K 38/48* | (2006.01) | |
| *A61K 31/198* | (2006.01) | |
| *A61K 38/46* | (2006.01) | |
| *A61K 38/47* | (2006.01) | |
| *A61P 1/18* | (2006.01) | |
| *A61P 5/48* | (2006.01) | |

(52) U.S. Cl.
CPC ............ *A61K 38/48* (2013.01); *A61K 31/198* (2013.01); *A61K 38/465* (2013.01); *A61K 38/47* (2013.01); *A61P 1/18* (2018.01); *A61P 5/48* (2018.01); *C12Y 301/01003* (2013.01); *C12Y 302/01001* (2013.01); *C12Y 304/24028* (2013.01)

(58) Field of Classification Search
CPC ... A61K 38/48; A61P 1/18; C12Y 301/01003; C12Y 302/01001; C12Y 304/24028
See application file for complete search history.

(56) References Cited

U.S. PATENT DOCUMENTS

| | | |
|---|---|---|
| 10,213,490 B2 | 2/2019 | Bromley et al. |
| 2006/0121017 A1 | 6/2006 | Margolin et al. |
| 2009/0110674 A1 * | 4/2009 | Loizou .................... A61K 35/74 424/94.2 |
| 2017/0182133 A1 | 6/2017 | Bromley et al. |
| 2018/0028454 A1 * | 2/2018 | Hall ...................... A61K 9/4858 |

FOREIGN PATENT DOCUMENTS

WO   WO-2016126970 A1 *   8/2016   ............. A61K 38/46

OTHER PUBLICATIONS

EFSA Panel on Food Contact Materials, Enzymes and Processing Aids (CEP); Silano et al., Safety evaluation of the food enzyme α-amylase from *Aspergillus oryzae* (strain DP-Bzb41). EFSA J. Nov. 27, 2019;17(11):e05899. doi: 10.2903/j.efsa.2019.5899. PMID: 32626183; PMCID: PMC7008918. (Year: 2019).*

Ajay Srivastava, Rajiv Lall, Jamil Talukder, Dan DuBourdieu, Ramesh C Gupta. Iron Transport Tocopheryl Polyethylene Glycol Succinate in Animal Health and Diseases. Molecules. Nov. 25, 2019;24(23):4289.

Aller Choice. Derm health. For support with dermatological sensitivities and overall skin health. Soft Chews for Dogs. Product Detail Sheet: Mar. 18, 2019. Clinics Choice, Acworth, GA 30101. Sold: Mar. 27, 2019.

Buccigrossi V, de Marco G et al. Lactoferrin induces concentration-dependent functional modulation of intestinal proliferation and differentiation, Pediatr Res. Apr. 2007; 61(4):410-4.

Bruni N., Teresa M., Capucchio et al. Antimicrobial Activity of Lactoferrin-Related Peptides and Applications in Human and Veterinary Medicine Molécules 2016, 21(6), 752.

Derm Choice—gel. Derm health. For support of overall dermotological health. Topical gel for dogs. Product Detail Sheet: Mar. 18, 2019. Clinics Choice, Acworth, GA 30101. Sold: Mar. 27, 2019.

Derm Choice—shampoo and conditioner. Derm health. For support of overall skin and coat health. Topical shampoo for Dogs. Product Detail Sheet: Mar. 18, 2019. Clinics Choice, Acworth, GA 30101. Sold: Mar. 27, 2019.

Flex Choice. Joint health. For support in overall mobility and healthy joint function. Powder for Cats. Product Detail Sheet: Mar. 18, 2019. Clinics Choice, Acworth, GA 30101. Sold: Mar. 27, 2019.

Flex Choice. Joint Health. For support in overall mobility and healthy joint function. Soft Chews for Dogs. Product Detail Sheet: Mar. 18, 2019. Clinics Choice, Acworth, GA 30101. Sold: Mar. 27, 2019.

Flora Choice—daily. Gut support. For support of daily and long term gut health. Powder for Cats & Dogs. Product Detail Sheet: Mar. 18, 2019. Clinics Choice, Acworth, GA 30101. Sold: Mar. 27, 2019.

Leocádio PC, Antunes MM, Teixeira LG, Leonel AJ, Alvarez-Leite JI, Machado DC, 20 Generoso SV, Cardoso VN, Correia MI. L-arginine pretreatment reduces intestinal mucositis as induced by 5-FU in mice. Nutr Cancer. 2015; 67(3):486-93.

Liver Choice. Hepatic support. For support of healthy hepatic function, and overall liver health. Soft Chews for Dogs. Product Detail Sheet: Mar. 18, 2019. Clinics Choice, Acworth, GA 30101. Sold: Mar. 27, 2019.

LysiPluc Choice. Immune support. For support of a healthy immune system and overall feline wellness. Powder for Cats. Product Detail Sheet: Mar. 18, 2019. Clinics Choice, Acworth, GA 30101. Sold: Mar. 27, 2019.

Ora Choice—pro. Dental health. For support of overall dental health. Dental Sticks for Dogs. Product Detail Sheet: Mar. 18, 2019. Clinics Choice, Acworth, GA 30101. Sold: Mar. 27, 2019.

(Continued)

*Primary Examiner* — Ruth A Davis

(74) *Attorney, Agent, or Firm* — Daniel A. Blasiole; DeWitt LLP

(57) ABSTRACT

A composition containing enzymes, L-arginine, and other components for treating exocrine pancreatic enzyme insufficiencies and gastrointestinal disorders in mammals. The compositions replace pancreatic enzymes while concurrently treating the side effects of small intestinal bacterial overgrowth and gastrointestinal mucosal degeneration that occurs with pancreatic enzyme loss. The composition can be mixed into animal feeds or sprayed onto extruded feeds prior to consumption.

16 Claims, No Drawings

(56) References Cited

OTHER PUBLICATIONS

Oti Choice. Derm health. For support of overall ear health. Topical for Dogs. Product Detail Sheet: Mar. 18, 2019. Clinics Choice, Acworth, GA 30101. Sold: Mar. 27, 2019.

Pancre Choice. Pancreatic support. For support in healthy pancreatic function vital to maintain overall health. Powder for Dogs. Product Detail Sheet: Mar. 18, 2019. Clinics Choice, Acworth, GA 30101. Sold: Mar. 27, 2019.

Pill Choice. Pill sleeves. Made with real peanut butter. Fits most tablets and capsules. Soft Chews for Dogs. Product Detail Sheet: Mar. 18, 2019. Clinics Choice, Acworth, GA 30101. Sold: Mar. 27, 2019.

Recov Choice. Energy support. Energy support. Helps maintain electrolyte balance. Manages the nutrient uptake. Gel for Dogs. Product Detail Sheet: Mar. 18, 2019. Clinics Choice, Acworth, GA 30101. Sold: Mar. 27, 2019.

Soetart N, Rochel D, Drut A, Jaillardon L. Serum cobalamin and folate as prognostic factors in canine exocrine pancreatic insufficiency: An observational cohort study of 299 dogs. Vet J. Nov. 2018; 243:15-20.

Talukder MJ, Harada E. Bovine lactoferrin protects lipopolysaccharide-induced diarrhea modulating nitric oxide and prostaglandin E2 in mice. Can J Physiol Pharmacol. Feb. 15, 2007; 85(2):2008.

Travel Choice. Gut support. For support of a normal, healthy digestive system. Gel for Dogs. Product Detail Sheet: Mar. 18, 2019. Clinics Choice, Acworth, GA 30101. Sold: Mar. 27, 2019.

Umathea, SN, N.I. Kochara,, N.S. Jainb, P.V. Dixit. Gastrointestinal dysfunction in diabetic rats relates with a decline in tissue l-arginine content and consequent low levels of nitric oxide. Nitric Oxide vol. 20, Issue 2, Mar. 1, 2009, pp. 129-133.

Velickovic K, Markelic M et al. Long-term dietary L-arginine supplementation increases endothelial nitric oxide synthase and vasoactive intestinal peptide immunoexpression in rat small intestine. Eur J Nutr. Apr. 2014; 53(3):813-21.

Wapnir RA, M A Wingertzahn, S Teichberg L-arginine in low concentration improves rat intestinal water and sodium absorption from oral rehydration solutions. Gut 1997; 40: 602-607.

\* cited by examiner

COMPOSITIONS AND METHODS FOR TREATING PANCREATIC ENZYME DEFICIENCIES IN MAMMALS

FIELD OF THE INVENTION

The present invention is directed to a method and compositions for treating exocrine pancreatic insufficiency (EPI) and secondary disorders in mammals.

BACKGROUND

Pancreatic enzyme insufficiencies are a problem particularly in young adults and perhaps 3 to 5% of dogs. Exocrine pancreatic insufficiency (EPI) in dogs is a gastrointestinal condition leading to a severe impairment of nutrient absorption. It is characterized by diarrhea or loose feces in dogs, but there are other issues. Treatment options have been limited to replacing enzymes and then treating the other side issues independently on a case-by-case basis.

The pancreas has two separate functions within the body stemming from the exocrine and endocrine pancreata. The endocrine pancreas secretes hormones, including insulin and glucagon, which regulate blood glucose metabolism. The exocrine pancreas secretes zymogens and active enzymes that ultimately aid in digestion. EPI is a condition of maldigestion and usually does not involve the endocrine pancreas.

Normally, the exocrine pancreas secretes many different zymogens for digesting carbohydrates, fats, and proteins. Some of the digestive enzymes secreted by the pancreas include various types of proteases, lipases and amylases. Protein digestion is catalyzed by the enzymes trypsin, chymotrypsin, and carboxypeptidase. These proteolytic digestive enzymes are initially released from the pancreas as the zymogens trypsinogen, chymotrypsinogen, and procarboxypeptidase, respectively, and are activated once they reach the small intestine. In the presence of chyme, enterocytes release enteropeptidase, which activates some of the trypsinogen. The newly formed trypsin assists in activating all three zymogens. This delayed activation prevents autodigestion of pancreatic proteins. Once activated, trypsin and chymotrypsin break down proteins into smaller peptides, while carboxypeptidase further processes some of these peptides into amino acids.

The exocrine pancreas facilitates carbohydrate digestion by secreting pancreatic amylase, which hydrolyzes most carbohydrates into disaccharides and some trisaccharides.

The exocrine pancreas facilitates fat digestion by releasing the enzymes pancreatic lipase, cholesterol esterase, and phospholipase as well as the zymogen procolipase, which is activated by trypsin to form colipase.

In both human and canine patients with EPI, inadequate production of digestive enzymes by the pancreatic acinar cells leads to maldigestion and malabsorption of nutrients. The persistence of undigested food within the small intestine often results in bacterial overgrowth, further compromising intestinal function. The causes of EPI include pancreatic acinar atrophy, chronic pancreatitis, pancreatic hypoplasia, and neoplasia. The most common cause of EPI in dogs is pancreatic acinar atrophy. The severity of this condition ranges from subclinical disease to a complete absence of secretory capacity. Pancreatic acinar atrophy is thought to be an immune-mediated condition that begins with lymphocytic pancreatitis. Selective destruction of acinar cells with replacement by atypical parenchyma, ductal structures, and adipose tissue is seen in the late stages of the disease.

In people, most cases of EPI are secondary to chronic pancreatitis, but the prevalence of cases of EPI that develop secondary to chronic pancreatitis in dogs is still unclear. Perhaps 3-5% of dogs might develop EPI. EPI can affect any breed, but German Shepherds may be overrepresented. The two breeds most commonly affected by pancreatic acinar atrophy, German Shepherds and rough-coated collies, are thought to have an autosomal recessive inherited form of the disease. Other breeds overrepresented among dogs with EPI due to any cause include Cavalier King Charles spaniels, chow chows, and English setters. The median age of dogs with EPI is variable, depending on the cause.

Dogs with EPI present with signs of maldigestion, primarily weight loss, despite an increased appetite, and diarrhea or loosely formed feces. The feces is usually yellow or gray, is increased in volume, and may appear undigested or pulpy. In most cases, fecal consistency is loosely formed, but dogs may experience severe watery diarrhea initially. The diarrhea is usually accompanied by steatorrhea, flatulence, and borborygmi. Some dogs with EPI also experience vomiting. Along with the weight loss, these dogs may have a poor coat. They may also seem nervous, aggressive, or irritable as a result of abdominal discomfort.

A diagnostic marker of EPI is abnormal serum trypsin-like immunoreactivity. In healthy animals, a small amount of the trypsinogen produced by the pancreas enters the blood circulation and can be measured in a blood sample by a test called trypsin-like immunoreactivity. Because trypsinogen is produced only by the pancreas, a low serum concentration of trypsinogen (i.e., trypsin-like immunoreactivity) is diagnostic for EPI. Elevated TLI concentrations, by contrast, are consistent with acute and chronic pancreatitis. Pancreatitis is one of the underlying causes of EPI.

While the loss of the enzymes is at the heart of the problem in EPI, several secondary issues occur. An important secondary issue of EPI is that 70% of dogs with EPI also develop a condition called small intestinal bacterial overgrowth (SIBO). When SIBO occurs, pathogenic bacteria gain hold in the gastrointestinal (GI) tract and cause numerous problems. This condition results in malabsorption of nutrients because pathogenic bacteria will compete with beneficial gastrointestinal bacteria for calories and nutrients, while concurrently producing toxins and thus damaging the intestinal mucosal and villi. This chain of events leads to major health issue for the patient. Treating this health issue is done as a side issue and is commonly overlooked by veterinarians focused on EPI.

A further issue associated with EPI is the degradation of the intestinal villi and mucosa in the GI tract. The intestinal villi are the actual structures responsible for nutrient absorption. Absorptive cells in the intestinal villi make different enzymes (lactase, sucrase, maltase etc.) that are essential for further digestion of foods. Damage to the villi and villi cells exacerbate the digestion and absorption issues associated with the EPI. Treatment options for repairing the GI tract under these circumstances has proven to be elusive.

Other issues associated with EPI are losses of vitamin B12. Vitamin B12 deficiencies lead to anemia and occur in 50-80% of dogs with EPI.

Zinc deficiencies are also associated with EPI. Zinc deficiencies are caused by diarrhea in EPI cases and cause loss of appetite. This contributes to further health issues in patients since zinc helps with the immune system and fighting infections.

The mainstay of treatment in dogs and other mammals with clinical EPI of any cause is pancreatic enzyme replacement. Commercially available preparations are generally derived from porcine pancreas and contain lipase, amylase, and protease for digestion of fats, carbohydrates, and proteins, respectively. Alternatively, chopped, raw bovine or porcine pancreas can be fed directly. These pancreatic enzyme replacements can have issues of microbial contamination potential since they come from animal sources. The contamination risks for spongiform encephalopathy, transmissible spongiform encephalopathy, and mammalian viruses associated with animal-sourced enzymes can occur. It would be preferable to minimize the disease risk of contamination. Furthermore, enzyme replacement alone does not directly address the other major secondary issues associated with EPI, namely, SIBO, villi degeneration, mucosal barrier function, vitamin B12 deficiency, and zinc deficiency, which can delay normal nutrient absorption and weight gain.

Accordingly, there is a need for directly and simultaneously addressing the secondary issues associated with EPI when treating the EPI itself. The current invention addresses this need.

SUMMARY OF THE INVENTION

The present invention is directed to addressing EPI and secondary gastrointestinal disorders such as SIBO and other GI disorders due to impaired mucosal barrier function. The invention accordingly provides compositions and methods suitable for treating these issues.

The compositions of the invention include active ingredients effective for treating EPI and the secondary gastrointestinal disorders in an inert carrier base.

The compositions can include enzymes as an active ingredient. The enzymes can comprise certain enzymes that are deficient in EPI, such as proteases, amylases, and lipases. The enzymes can be used to treat EPI in mammals such as dogs by predigesting foods commonly consumed by the mammals. The enzymes can be mixed with food prior to the mammal consuming the food. This permits the proteins, carbohydrates, and lipids in the food to be partially digested prior to consumption, thus allowing the mammal to obtain the nutrients in a predigested format.

The compositions can also include L-arginine as an active ingredient. The L-arginine is included as a nitric oxide precursor to help develop and maintain normal mucosal barrier integrity, stimulate villus growth, and regenerate the GI tract. The production of nitric oxide from the exogenous source of L-arginine in combination with the exogenous source of enzymes in the compositions of the invention stimulates gut health and eliminates pathogenic bacteria in animals with EPI and SIBO. Thus, the combination of enzymes with L-arginine in the compositions of the invention not only treats the loss of enzymes in EPI but also eliminates pathogenic bacteria and directly repairs the GI tract as well.

The compositions can also include vitamin B12 as an active ingredient. Vitamin B12 helps in the normal functioning of the immune system, maintaining or increasing appetite, and gaining weight. In addition, it helps keep the body's nerve and blood cells healthy and helps make DNA, the genetic material in all cells. Vitamin B12 also helps prevent a type of anemia called megaloblastic anemia that makes animals tired and weak.

The compositions can also include a non-heme, iron-binding glycoprotein as an active ingredient. An exemplary non-heme, iron-binding glycoprotein is lactoferrin. The non-heme, iron-binding glycoprotein helps to destroy pathogenic bacteria in the GI tract that cause MO associated with the EPI.

Accordingly, some versions of the invention are directed to an oral ingestible composition for treating exocrine pancreatic insufficiency and a secondary gastrointestinal disorder thereof in a mammal. The composition in some versions comprises active ingredients in an inert carrier base. The active ingredients in some versions comprise a protease, a lipase, an amylase, and L-arginine.

In some versions, the protease comprises an enzyme with an International Union of Biochemistry (IUB) classification of 3.4.24.28. In some versions, the protease comprises a microbial enzyme. In some versions, the protease is microbially produced. In some versions, the protease is present in the composition an amount from about 200,000 USP Units/g to about 800,000 USP Units/g.

In some versions, the lipase an enzyme with an International Union of Biochemistry (IUB) classification of 3.1.1.3. In some versions, the lipase comprises a microbial enzyme. In some versions, the lipase comprises microbially produced. In some versions, the lipase is present in the composition in an amount from about 35,000 USP Units/g to about 140,000 USP Units/g.

In some versions, the amylase comprises an enzyme with an International Union of Biochemistry (IUB) classification of 3.2.1.1. In some versions, the amylase comprises a microbial enzyme. In some versions, the amylase is microbially produced. In some versions, the amylase is present in the composition in an amount from about 230,000 USP Units/g to about 920,000 USP Units/g.

In some versions, the L-arginine is present in the composition in an amount from about 2.5% w/w to about 10% w/w.

In some versions, the active ingredients further comprise vitamin B12. In some versions, the vitamin B12 is present in the composition in an amount of about 0.01% w/w to about 0.05% w/w.

In some versions, the active ingredients further comprise a non-heme, iron-binding glycoprotein. In some versions, the non-heme, iron-binding glycoprotein is selected from the group consisting of ferritin, lactoferrin, transferrin, and ovotransferrin. In some versions, the non-heme, iron-binding glycoprotein is at least partially present in apo form. In some versions, the non-heme, iron-binding glycoprotein is present in the composition in an amount from about 2.5% w/w to about 10% w/w.

In some versions, the inert carrier base is present in the composition in an amount from about 12.5% w/w to about 50% w/w.

In some versions, the oral ingestible composition is in a powder form.

In some versions, the active ingredients are present in the composition in amounts effective to treat the exocrine pancreatic insufficiency and the secondary gastrointestinal disorder in the mammal.

The methods of the invention improve on current enzyme replacement treatment options by treating the EPI along with the secondary issues in a simple-to-use approach. The methods administering enzymes and other active ingredients to animals with EPI to treat the EPI along with concurrent treatment of GI disorders such as SIBO, gastroenteritis, and mucositis. It is therefore an object of the invention to provide a simple method of administering enzymes and other active components to animals with EPI that also allows for concurrent treatment of GI disorders such as SIBO and gastroenteritis and mucositis.

Accordingly, some versions of the invention are directed to a method for treating exocrine pancreatic insufficiency and a secondary gastrointestinal disorder thereof in a mammal.

The method in some versions comprises administering a composition of the invention to the mammal in an amount effective to treat the exocrine pancreatic insufficiency and the secondary gastrointestinal disorder thereof in the mammal.

In some versions, the composition is in a powder form, the composition is added in powder form to or mixed with food prior to the administering to thereby form a composition-supplemented food, and the administering comprises feeding the composition-supplemented food to the mammal.

In some versions, the composition is in a powder form, the composition in powder form is mixed with a liquid to thereby form a composition-supplemented liquid, the composition-supplemented liquid is added to or mixed with food prior to the administering to thereby form a composition-supplemented food, and the administering comprises feeding the composition-supplemented food to the mammal.

In some versions, the composition is administered to the mammal in an amount and for a time effective to elicit at least one of the following effects: a normalization of fasting blood cobalamin levels; a normalization of fasting blood folate levels; a normalization of fasting blood trypsin-like immunoreactivity levels; a decrease in dysbiosis index; and an increase in weight.

In some versions, the secondary disorder of the exocrine pancreatic insufficiency that is treated comprises small intestinal bacterial overgrowth, gastroenteritis, and mucositis.

The objects and advantages of the invention will appear more fully from the following detailed description of the preferred embodiment of the invention.

DETAILED DESCRIPTION OF THE INVENTION

The invention is generally directed to an oral ingestible compositions and methods for treating EPI and secondary GI disorders in a mammal. The compositions can comprise a therapeutically effective amount of active ingredients to treat EPI and secondary GI disorders. The active ingredients can comprise enzymes that are required to digest proteins, lipids and carbohydrates such as starch in animals with EPI, among other active ingredients effective for treating the secondary disorders.

Protease

Proteases are enzymes capable of catabolizing proteins into shorter fragments by splitting the peptide bonds that link amino acid residues. Proteases suitable for the compositions of the invention include enzymes that individually or collectively exhibit protease activity as defined according to the test provided in the examples under the section entitled "Protease Activity and USP Units Thereof."

Suitable proteases for the compositions of the invention include serine proteases, cysteine proteases, threonine proteases, aspartic proteases, glutamic proteases, metalloproteases, asparagine peptide lyases. Suitable proteases can include exopeptidases such as aminopeptidases and carboxypeptidase A, among others. Other suitable proteases can include endopeptidases such as trypsin, chymotrypsin, pepsin, papain, and elastase, among others. The proteases can be neutral proteases, acid proteases, and/or basic proteases (alkaline proteases).

The protease can be included in the composition in any amount. Exemplary amounts include amount from about 1 USP Units/g to about 4,000,000 USP Units/g. Exemplary ranges include from about 40,000 USP Units/g to about 4,000,000 USP Units/g, from about 80,000 USP Units/g to about 2,000,000 USP Units/g, from about 120,000 USP Units/g to about 1,300,000 USP Units/g, or from about 200,000 USP Units/g to about 800,000 USP Units/g. The USP Units of protease activity for compositions can be determined according to the test entitled "Protease Activity and USP Units Thereof" provided in the examples.

In some versions, the protease comprises an enzyme with an International Union of Biochemistry (IUB) classification of 3.4.24.28. An exemplary enzyme with an IUB classification of 3.4.24.28 is the Neutral Protease derived from *Bacillus subtilis* obtainable commercially from Bio-Cat (Troy, VA).

Lipase

Lipases are enzymes capable of catalyzing the hydrolysis of lipids (fats). Examples of suitable lipases include any of the various esterases that cleave fatty acids from other lipid or non-lipid moieties. Most lipases act at one or more positions (A1, A2, or A3) on the glycerol backbone of a lipid substrate. Lipases suitable for the compositions of the invention include enzymes that individually or collectively exhibit lipase activity as defined according to the test provided in the examples under the section entitled "Lipase Activity and USP Units Thereof."

Suitable lipases for the compositions of the invention include triacylglycerol lipases, lipoprotein lipases, cholesterol esterases, phospholipases, and sphingomyelinases, among others.

The lipase can be included in the composition in any amount. Exemplary amounts include amounts from about 1 USP Units/g to about 720,000 USP Units/g. Exemplary ranges include from about 7,200 USP Units/g to about 720,000 USP Units/g, from about 14,400 USP Units/g to about 360,000 USP Units/g, from about 20,000 USP Units/g to about 240,000 USP Units/g, or from about 36,000 USP Units/g to about 144,000 USP Units/g.

In some versions, the lipase comprises an enzyme with an International Union of Biochemistry (IUB) classification of 3.1.1.3. An exemplary enzyme with an IUB classification of 3.1.1.3 is the Fungal Lipase derived from *Rhizopus oryzae* obtainable commercially from Bio-Cat (Troy, VA).

Amylase

Amylases are enzymes that catalyzes the hydrolysis of starches. Amylases suitable for the compositions of the invention include enzymes that individually or collectively exhibit amylase activity as defined according to the test provided in the examples under the section entitled "Amylase Activity and USP Units Thereof."

Suitable amylases for the compositions of the invention include α-amylases, β-amylases, and γ-amylases.

The amylase can be included in the composition in any amount. Exemplary amounts include amounts from about 1 USP Units/g to about 4,600,000 USP Units/g. Exemplary ranges include from about 46,000 USP Units/g to about 4,600,000 USP Units/g, from about 92,000 USP Units/g to about 2,300,000 USP Units/g, from about 140,000 USP Units/g to about 1,500,000 USP Units/g, or from about 230,000 USP Units/g to about 920,000 USP Units/g.

In some versions, the amylase comprises an enzyme with an International Union of Biochemistry (IUB) classification of 3.2.1.1. An exemplary enzyme with an IUB classification of 3.2.1.1 is the Bacterial Amylase derived from *Bacillus amyloliquefaciens* obtainable commercially from Bio-Cat (Troy, VA).

Enzyme Sources

The enzymes of the invention are preferably sourced from microbial sources rather than animal sources. This allows for less chance of contamination of transmissible spongiform encephalopathy and mammalian viruses associated with animal-sourced enzymes. In addition, and unexpectantly, the use of microbial sources of enzymes give better digestion rates of feeds as compared to animal sourced enzymes. For the purposes herein, *Rhizopus oryzae* is considered herein to be a microbe.

The enzymes can be produced in microbial fermentations. After the fermentation, the enzymes can be dried into powders by methods known in the art.

The enzymes of the invention can also be microbial enzymes. The term "microbial enzymes" refers to enzymes that include a sequence of an enzyme from a microbe as found in nature, or a sequence at least 95% identical to the sequence of the enzyme as found in nature.

L-Arginine:

The compositions of the invention can include L-arginine as another active ingredient. L-arginine is an amino acid. L-arginine is included in the compositions of the invention to help animals repair the gut mucosa damaged by EPI/SIBO and help overall animal health.

L-arginine helps regulate mucosal barrier integrity by working to produce nitric oxide under physiological conditions and counter the increase in mucosal permeability associated with acute pathophysiological states. Arginine is the endogenous precursor of nitric oxide in animals. Nitric oxide (NO) regulates mucosal barrier integrity under physiological conditions, counters the increase in mucosal permeability associated with acute pathophysiological states such as found in EPI with SIBO, and reduces acute inflammation. The potential mechanisms of actions of nitric oxide in companion animals include maintenance of blood flow, inhibition of platelet and leukocyte adhesion and/or aggregation within the vasculature, modulation of mast cell reactivity, and scavenging of reactive oxygen metabolites such as superoxide. Nitric oxide produced from the exogenous arginine provided by the compositions of the invention has the same effects.

L-arginine can positively impact SIBO, gastroenteritis, and/or intestinal mucositis by promoting partial mucosal recovery, reducing inflammation, and improving intestinal permeability.

The amylase can be included in the composition in any amount and can be adapted to the specific needs of the animal. Exemplary amounts include amounts from about 0.001% w/w to about 50% w/w. Exemplary ranges include from about 0.5% w/w to about 50% w/w, from about 1% w/w to about 25% w/w, from about 1.5% w/w to about 15% w/w, or from about 2.5% w/w to about 10% w/w.

Non-Heme, Iron-Binding Glycoprotein

The compositions of the invention can include a non-heme, iron-binding glycoprotein as another active ingredient. Non-heme, iron-binding glycoproteins are glycoproteins that do not contain a heme group but still bind iron. Exemplary non-heme, iron-binding glycoproteins include ferritin, lactoferrin, transferrin, and ovotransferrin.

Lactoferrin is a multifunctional iron glycoprotein that exerts a broad-spectrum primary defense activity against bacteria, fungi, protozoa and viruses. Its iron-sequestering property is at the basis of the bacteriostatic effect since bacteria require iron to survive. Lactoferrin can be purified from milk or produced recombinantly.

Ferritin is a universal intracellular protein that stores iron and releases it in a controlled fashion. It is a globular protein complex of 24 protein subunits forming a nanocage with multiple metal-protein interactions. The protein is produced by almost all living organisms, including algae, bacteria, higher plants, and animals. In humans, it acts as a buffer against iron deficiency and iron overload. Ferritin is found in most tissues as a cytosolic protein, but small amounts are secreted into the serum where it functions as an iron carrier.

Transferrin is an iron-binding blood plasma glycoprotein that control the level of free iron (Fe) in biological fluids. In humans, transferrin is composed of a polypeptide chain containing 679 amino acids and two carbohydrate chains. The protein is composed of alpha helices and beta sheets that form two domains. The N- and C-terminal sequences are represented by globular lobes and between the two lobes is an iron-binding site. The amino acids which bind the iron ion to the transferrin are identical for both lobes: two tyrosines, one histidine, and one aspartic acid. For the iron ion to bind, an anion is required, preferably carbonate ($CO_2^{-3}$).

Ovotransferrin (conalbumin) is a glycoprotein of egg white albumen. Egg white albumen is composed of multiple proteins. Ovotransferrin is the most heat reliable protein of them all. It typically has a molecular weight of 76,000 Daltons and contains about 700 amino acids. Ovotransferrin makes up approximately 13% of egg albumen. Ovotransferrin or conalbumin belong to the transferrin protein family and is endowed with both iron-transfer and protective activities. Ovotransferrin has similar antibacterial properties and protective roles as lactoferrin.

Compositions of the invention containing a non-heme, iron-binding glycoprotein can be placed into feed that is consumed by an animal such that the non-heme, iron-binding glycoprotein is passed into the GI tract to kill pathogens in the gut of animals that have SIBO. In order to bind iron in the intestines, the non-heme, iron-binding glycoprotein is preferably at least partially included in the compositions in an apo form (the form not bound to iron).

Non-heme, iron-binding glycoproteins can be sensitive to the lower pH acidic environment in the stomach. In use, the non-heme, iron-binding glycoprotein in the compositions of the invention must pass through the stomach in order to get to the intestines where it can be utilized. Encapsulation of the non-heme, iron-binding glycoprotein will help ensure survival in the passage through the GI tract for optimal effect. Accordingly, in some versions of the invention the non-heme, iron-binding glycoprotein is encapsulated.

The non-heme, iron-binding glycoprotein can be included in the composition in any amount and can be adapted to the specific needs of the animal. Exemplary amounts include amounts from about 0.001% w/w to about 50% w/w. Exemplary ranges include from about 0.5% w/w to about 50% w/w, from about 1% w/w to about 25% w/w, from about 1.5% w/w to about 15% w/w, or from about 2.5% w/w to about 10% w/w.

Vitamin B12

The compositions of the invention can include vitamin B12 as another active ingredient. Vitamin B12 helps in the normal functioning of the immune system, red blood cell and hemoglobin formation, maintaining or increasing appetite, and gaining weight.

The vitamin B12 can be included in the composition in any amount and can be adapted to the specific needs of the animal. Exemplary amounts include amounts from about 0.0001% w/w to about 10% w/w. Exemplary ranges include from about 0.001% w/w to about 1% w/w, from about 0.0025% w/w to about 0.25% w/w, from about 0.005% w/w to about 0.125% w/w, from about 0.01% w/w to about 0.1% w/w or from about 0.01% w/w to about 0.05% w/w.

Minerals

The compositions of the invention can include one or more minerals as additional active ingredients. Minerals play important roles in many biochemical functions in the body. Deficiencies of minerals can lead to problems in the immune system. In EPI, zinc can be lost. However, supplementation of zinc can help correct these problems since zinc helps with the immune system and fighting infections. As absorption of chelated minerals to amino acids or other substances is enhanced, the minerals included in the compositions of the invention can comprise chelated minerals. Exemplary minerals that can be included in the compositions to benefit the immune system include copper, zinc, manganese, and molybdenum.

The minerals can be included in the composition in any amount and can be adapted to the specific needs of the animal. Exemplary amounts include from 0.1 mg/kg to 2 mg/kg for copper, from 100 mg/kg to 300 mg/kg for zinc, from 0.05 mg/kg to 0.2 mg/kg for manganese, and from 0.0003 mg/kg to 0.05 mg/kg for molybdenum.

Vitamins

The compositions of the invention can include one or more vitamins in addition to or as an alternative to vitamin B12 as additional active ingredients. Vitamins are necessary for various different biochemical reactions in the body including as co-factors. They often work in conjunction with minerals and enzymes to assure normal digestion, reproduction, muscle and bone growth and function, healthy skin and hair, clotting of blood, and the use of fats, proteins, and carbohydrates by the body. For example, vitamin E isomers (mixed tocopherols) are antioxidants that help protect animals from free radical damage.

Any vitamin known in the art may be included in the compositions of the invention. Particular vitamins may be provided according to the nutritional requirements of the target animal. Suitable vitamins include both water soluble and/or fat-soluble vitamins. Exemplary water-soluble vitamins include any or all the B vitamins (Vitamin $B_1$, $B_2$, $B_3$, $B_4$, $B_5$, $B_6$, $B_7$, $B_8$, $B_9$, $B_{10}$, $B_{11}$, and $B_{12}$) and/or Vitamin C. Exemplary fat-soluble vitamins include Vitamin A, Vitamin D, Vitamin E, and Vitamin K.

The minerals can be included in the composition in any amount and can be adapted to the specific needs of the animal. As an example, each vitamin may be included in an amount of from about 0.001% w/w to about 10% w/w, from about 0.01% w/w to about 5% w/w, or from about 0.5% to about 1% w/w.

Antioxidants

The compositions of the invention can include one or more antioxidants as additional active ingredients. Examples of suitable antioxidants include alpha-tocopherol, alpha-tocopherol acetate, butylated hydroxytoluene (BHT), ascorbic acid, mixed tocopherols, propyl gallate, and mixtures thereof. The antioxidant may be included in an amount of from about 0% to about 0.3% w/w, from about 0.025% to about 0.2% w/w, or from about 0.05% to 0.15% w/w.

Compositional Form and Inert Carrier Base

The compositions of the invention can be provided in any number of forms. Such forms can include powders, pastes, tablets, gels, liquids, and soft dough delivery systems. In preferred versions of the invention, the composition is provided in the form of a powder.

The compositions of the invention can include an inert carrier base for the active ingredients. The particular carrier base employed depends on the form in which the composition is provided.

A powder base, for example, is used for providing the composition in powder form. Examples of powder bases include poultry liver flavor powder, Tixosil, corn starch, silicone dioxide, verxite, talc, attapulgite clay, calcium silicate, calcium stearate, diatomaceous earth, ethyl cellulose, hydrophobic silica, iron ammonium citrate, kaolin, monmorillonite clays, pyrophyllite, sodium silico aluminate, and xanthan gum.

The powder base may comprise a plant powder, an animal powder, or both a plant and an animal powder. Plant powders are powders derived from plants, such as flours or other powders. The flours may be whole flours or flours which have had fractions, such as the germ fraction or the husk fraction, removed. Non-limiting examples of suitable plant powders include soy flour, wheat flour, whole wheat flour, whole wheat fine flour, wheat feed flour, wheat gluten, pre-gel wheat flour, soy protein concentrate, oat flour or powder, barley powder or flour, brown rice flour or powder, dried whey powder, carrot powder, cherry powder, pineapple powder, and alfalfa herb powder. Animal powders are powders derived from animals and can include dehydrated meat byproducts, such as liver powder.

The powder base may include a starch. Starches from various sources are known in the art. Suitable starches can be obtained from tuberous foodstuffs, such as potatoes, tapioca, and the like. Other suitable starches can be obtained upon grinding cereal grains such as corn, oats, wheat, milo, barley, rice, and others.

Bases for paste, tablet, gel, liquid, and soft dough compositional forms are well known in the art.

The inert carrier base may comprise a flavoring to enhance the palatability of the composition. The flavoring is preferably food grade quality. Sweeteners constitute one type of suitable flavoring. Examples of suitable sweeteners include such sugars as xylose, ribose, sucrose, mannose, galactose, fructose, dextrose, and maltose. Other suitable sweeteners include molasses, honey, maple syrup, and fruit flavoring. The sweeteners may be in powdered, granulated, or liquid form, depending on the form in which the composition is provided. Natural or synthetic sweeteners are suitable. Preferred sweeteners include powdered sugar and dry molasses. Other suitable flavorings include carob, peanuts, garlic, and herbs such as, parsley, celery, peppermint, and spearmint. Natural and synthetic flavoring oils can also be included as a flavoring. Examples of flavoring oils include anise oil, spearmint oil, peppermint oil, cinnamon oil, wintergreen oil, citrus oils, such as lemon, orange, grape, lime, and grapefruit oils. Other suitable flavorings include fruit essences such as apple, strawberry, cherry, and pineapple essences, among others.

The inert carrier base may comprise a preservative to prevent or retard growth of microorganisms and fungi. Suitable preservatives include potassium sorbate, methylparaben, propylparaben, sodium benzoate, calcium propionate, or combinations thereof. A preferred preservative comprises a combination of potassium sorbate, methylparaben, and propylparaben.

The inert carrier may comprise salts. Examples of salts include potassium or calcium salts such as sodium chloride, potassium chloride, calcium chloride, or potassium citrate, among others.

Preparation

The individual ingredients in the composition of the invention can be mixed together in a standard mixing apparatus. The dry powders are preferably mixed initially. Encapsulation of the ingredients prior to mixing together in the invention can be done using methods known in the art.

Encapsulation helps to protect the ingredients from degradation while the invention is sitting on the shelf waiting to be used. In addition, encapsulation can help the ingredients make it through the stomach acids and not be degraded and then subsequently absorbed and utilized in the GI tract of the animal. There are numerous methods known in the art to encapsulate ingredients. Most of encapsulates are spray-dried ones, others are prepared by spray-chilling, freeze-drying, melt extrusion and melt injection. Molecular inclusion in cyclodextrins and liposomal vesicles such as from chitosan and alginate are also used. The current invention can also employ any of these encapsulation methods to help protect the ingredients.

Methods

The compositions of the invention can be used in methods for treating exocrine pancreatic insufficiency and secondary gastrointestinal disorders thereof. The methods can comprise administering a composition of the invention to a mammal in an amount effective to treat the exocrine pancreatic insufficiency and one or more secondary gastrointestinal disorders thereof. The secondary gastrointestinal disorders can include small intestinal bacterial overgrowth, gastroenteritis, mucositis, and gastrointestinal inflammation, among others.

When the compositions of the invention are provided in powder form, the compositions can be administered in any of a number of ways. In one method, the composition is fed directly to the animal. In another method, the composition is added to or mixed with food to thereby form a composition-supplemented food. The composition-supplemented food is then fed to the animal. In another method, the composition is mixed with a liquid to thereby form a composition-supplemented liquid. The composition-supplemented liquid is added to or mixed with food to thereby form a composition-supplemented food. The composition-supplemented food is then fed to the animal. "Food" as used herein refers to any orally ingestible substance that provides hydration or caloric sustenance to an animal, in any form. Exemplary forms include liquid, solid, or semi-solid (e.g., gel, paste, dough) forms.

Addition of the compositions directly to foods prior to consumption can permit the starches, proteins, and lipids to start being digested before the food enters the digestive tract. This allows a partially predigested meal to be consumed by the animal that has EPI.

The compositions are preferably administered to the mammal in an amount and for a time effective to elicit a normalization of in fasting blood cobalamin levels, a normalization of fasting blood folate levels, a normalization of fasting blood trypsin-like immunoreactivity levels, a normalization of dysbiosis index, and an increase in weight. The term "normalization" used in reference to a given level refers either to an increase or a decrease in the given level to be within a normal range. In dogs, the normal range for fasting blood cobalamin levels is 251-908 ng/L; the normal range for fasting blood folate levels is 7.7-24.4 µg/L; the normal range for fasting blood trypsin-like immunoreactivity levels (cTLI) is 5.7-45.2 µg/L; and the normal range of dysbiosis index is <0. The normal range for TLI levels in cats is 12-82 µg/L. Normal ranges for these various levels in other mammals are well known in the art. In some versions, the normalizations comprise an increase in fasting blood cobalamin levels, an increase in fasting blood folate levels, and/or a decrease in dysbiosis index.

It is predicted that the combination of L-arginine and/or other active ingredients with the enzymes in the compositions and methods of the invention will lead to faster amelioration of the effects associated with EPI and secondary gastrointestinal disorders than equivalent compositions and methods lacking the L-arginine and/or other active ingredients. For example, it is predicted that the combination of L-arginine and/or other active ingredients with the enzymes in the compositions and methods of the invention will result in an increase in fasting blood cobalamin levels, an increase in fasting blood folate levels, a normalization of blood trypsin-like immunoreactivity levels, a decrease in dysbiosis index, and/or an increase in weight in a shorter time frame than equivalent compositions and methods lacking the L-arginine and/or other active ingredients. It is also predicted that the combination of L-arginine and/or other active ingredients with the enzymes in the compositions and methods of the invention will result in a greater increase in fasting blood cobalamin levels, a greater increase in fasting blood folate levels, a greater decrease in dysbiosis index, and/or a greater increase in weight in the same time frame than equivalent compositions and methods lacking the L-arginine and/or other active ingredients.

EXAMPLES

Example 1. Protease Activity and USP Units Thereof

One USP Unit of protease activity is contained in the amount of composition that under the conditions of the following assay hydrolyzes casein at an initial rate such that there is liberated per minute an amount of peptides not precipitated by trichloroacetic acid that gives the same absorbance at 280 nm as 15 nmol of tyrosine.

Casein Substrate: Place 1.25 g of finely powdered casein in a 100-mL conical flask containing 5 mL of water, shake to form a suspension, add 10 mL of 0.1 N sodium hydroxide, shake for 1 minute, add 50 mL of water, and shake for about 1 hour to dissolve the casein. The resulting solution should have a pH of about 8. If necessary, adjust the pH to about 8, using 1 N sodium hydroxide or 1 N hydrochloric acid. Transfer the solution to a 100-mL volumetric flask, dilute with water to volume, and mix. Use this substrate on the day it is prepared.

Buffer Solution: Dissolve 6.8 g of monobasic potassium phosphate and 1.8 g of sodium hydroxide in 950 mL of water in a 1000-mL volumetric flask, adjust to a pH of 7.5±0.2, using 0.2 N sodium hydroxide, dilute with water to volume, and mix. Store this solution in a refrigerator.

Trichloroacetic Acid Solution: Dissolve 50 g of trichloroacetic acid in 1000 mL of water. Store this solution at room temperature.

Filter Paper: Determine the suitability of the filter paper by filtering a 5-mL portion of Trichloroacetic Acid Solution through the paper and measuring the absorbance of the filtrate at 280 nm, using an unfiltered portion of the same Trichloroacetic Acid Solution as the blank: the absorbance is not more than 0.04. If the absorbance is more than 0.04, the filter paper may be washed repeatedly with Trichloroacetic Acid Solution until the absorbance of the filtrate, determined as above, is not more than 0.04.

Standard Test Dilution: Add about 100 mg of USP Pancreatin Amylase and Protease Reference Standard, accurately weighed, to 100.0 mL of Buffer Solution, and mix by shaking intermittently at room temperature for about 25 minutes. Dilute quantitatively with Buffer Solution to obtain a concentration of about 2.5 USP Units of protease activity per mL, based on the potency declared on the label of the Reference Standard.

Assay Test Dilution: Weigh accurately about 100 mg of composition into a mortar. Add about 3 mL of Buffer Solution, and triturate for 5 to 10 minutes. Transfer the mixture with the aid of Buffer Solution to a 100-mL volumetric flask, dilute with Buffer solution to volume, and mix. Dilute quantitatively with Buffer Solution to obtain a dilution that corresponds in activity to that of the Standard Test Dilution.

Procedure: Label test tubes in duplicate $S_1$, $S_2$, and $S_3$ for the standard series, and U for the sample. Pipet into tubes $S_1$ 2.0 mL, into $S_2$ and U 1.5 mL, and into $S_3$ 1.0 mL of Buffer Solution Pipet into tubes $S_1$ 1.0 mL, into $S_2$ 1.5 mL, and into $S_3$ 2.0 mL of the Standard Test Dilution. Pipet into tube U 1.5 mL of the Assay Test Dilution. Pipet into one tube each of $S_1$, $S_2$, $S_3$, and U 5.0 mL of Trichloroacetic Acid Solution, and mix. Designate these tubes as $S_{1B}$, $S_{2B}$, $S_{3B}$, and $U_B$, respectively. Prepare a blank by mixing 3 mL of Buffer Solution and 5 mL of Trichloroacetic Acid Solution in a separate test tube marked B. Place all the tubes in a 40° C. water bath, insert a glass stirring rod into each tube, and allow for temperature equilibration. At zero time, add to each tube, at timed intervals, 2.0 mL of the Casein Substrate, preheated to the bath temperature, and mix. Sixty minutes, accurately timed, after the addition of the Casein Substrate stop the reaction in tubes $S_1$, $S_2$, $S_3$, and U by adding 5.0 mL of Trichloroacetic Acid Solution at the corresponding time intervals, stir, and remove all the tubes from the bath. Allow to stand for 10 minutes at room temperature for complete protein precipitation, and filter. The filtrates must be free from haze. Determine the absorbances of the filtrates, in 1-cm cells, at 280 nm, with a suitable spectrophotometer, using the filtrate from the blank (tube 8) to set the instrument.

Calculation of Potency: Correct the absorbance values for the filtrates from tubes $S_1$, $S_2$, and $S_3$ by subtracting the absorbance values for the filtrates from tubes $S_{1B}$, $S_{2B}$, and $S_{3B}$, respectively, and plot the corrected absorbance values against the corresponding volumes of the Standard Test Dilution used. From the curve, using the corrected absorbance value ($U-U_B$) for the composition taken, and taking into consideration the dilution factors, calculate the protease activity, in USP Units, of the composition taken by comparison with that of the Standard, using the protease activity stated on the label of USP Pancreatin Amylase and Protease Reference Standard.

Example 2. Lipase Activity and USP Units Thereof

One USP Unit of lipase activity is contained in the amount of composition that liberates 1.0 pEq of acid per minute at a pH of 9.0 and 37° C. under the conditions of the following assay.

Acacia Solution: Centrifuge a solution of acacia (1 in 10) until clear. Use only the clear solution.

Olive Oil Substrate: Combine 165 mL of Acacia Solution, 20 mL of olive oil, and 15 g of crushed ice in the cup of an electric blender. Cool the mixture in an ice bath to 5° C., and homogenize at high speed for 15 minutes, intermittently cooling in an ice bath to prevent the temperature from exceeding 30° C. Test for suitability of mixing as follows. Place a drop of the homogenate on a microscope slide, and gently press a cover slide in place to spread the liquid. Examine the entire field under high power (43× objective lens and 5× ocular), using an eyepiece equipped with a calibrated micrometer. The substrate is satisfactory if 90% of the particles do not exceed 2 pm in diameter and none exceeds 10 pm in diameter.

Buffer Solution: Dissolve 60 mg of tris(hydroxymethyl) aminomethane and 234 mg of sodium chloride in water to make 100 mL.

Bile Salts Solution: Prepare a solution to contain 80.0 mg of USP Bile Salts Reference Standard in each mL.

Standard Test Dilution: Suspend about 200 mg of USP Pancreatin Lipase Reference Standard, accurately weighed, in about 3 mL of cold water in a mortar, triturate for 10 minutes, and add cold water to a volume necessary to produce a concentration of 8 to 16 USP Units of lipase activity per mL, based upon the declared potency on the label of the USP Reference Standard. Maintain the suspension at 4° C., and mix before using. For each determination withdraw 5 to 10 mL of the cold suspension, and allow the temperature to rise to 20° C. before pipeting the exact volume.

Assay Test Dilution: Suspend about 200 mg of composition, accurately weighed, in about 3 mL of cold water in a mortar, triturate for 10 minutes, and add cold water to a volume necessary to produce a concentration of 8 to 16 USP Units of lipase activity per mL, based upon the estimated potency of the test material. Maintain the suspension at 4° C., and mix before using. For each determination withdraw 5 to 10 mL of the cold suspension, and allow the temperature to rise to 20° C. before pipeting the exact volume.

Procedure: Mix 10.0 mL of Olive Oil Substrate, 8.0 mL of Buffer Solution, 2.0 mL of Bile Salts Solution, and 9.0 mL of water in a jacketed glass vessel of about 50-mL capacity, the outer chamber of which is connected to a thermostatically controlled water bath. Cover the mixture, and stir continuously with a mechanical stirring device. With the mixture maintained at a temperature of 37±0.1° C., add 0.1 N sodium hydroxide VS, from a microburet inserted through an opening in the cover, and adjust to a pH of 9.20 potentiometrically using a calomel-glass electrode system. Add 1.0 mL of the Assay Test Dilution, and then continue adding the 0.1 N sodium hydroxide VS for 5 minutes to maintain the pH at 9.0. Determine the volume of 0.1 N sodium hydroxide VS added after each minute.

In the same manner, titrate 1.0 mL of Standard Test Dilution.

Calculation of Potency: Plot the volume of 0.1 N sodium hydroxide VS titrated against time. Using only the points which fall on the straight-line segment of the curve, calculate the mean acidity released per minute by the test specimen and the Standard. Taking into consideration the dilution factors, calculate the lipase activity, in USP Units, of the composition taken by comparison to the activity of the Standard, using the lipase activity stated on the label of USP Pancreatin Lipase Reference Standard.

Example 3. Amylase Activity and USP Units Thereof

One USP Unit of amylase activity is contained in the amount of composition that decomposes starch at an initial rate such that 0.16 p Eq of glycosidic linkage is hydrolyzed per minute under the conditions of the following assay.

pH 6.8 Phosphate Buffer: On the day of use, dissolve 13.6 g of monobasic potassium phosphate in water to make 500 mL of solution. Dissolve 14.2 g of anhydrous dibasic sodium phosphate in water to make 500 mL of solution. Mix 51 mL of the monobasic potassium phosphate solution with 49 mL of the dibasic sodium phosphate solution. If necessary, adjust by the dropwise addition of the appropriate solution to a pH of 6.8.

Substrate Solution: On the day of use, stir a portion of purified soluble starch equivalent to 2.0 g of dried substance with 10 mL of water, and add this mixture to 160 mL of boiling water. Rinse the beaker with 10 mL of water, add it to the hot solution, and heat to boiling, with continuous mixing. Cool to room temperature, and add water to make 200 mL.

Standard Preparation: Weigh accurately about 20 mg of USP Pancreatin Amylase and Protease Reference Standard into a suitable mortar. Add about 30 mL of pH 6.8 phosphate buffer, and triturate for 5 to 10 minutes. Transfer the mixture with the aid of pH 6.8 phosphate buffer to a 50-mL volumetric flask, dilute with pH 6.8 phosphate buffer to volume, and mix. Calculate the activity, in USP Units of amylase activity per mL, of the resulting solution from the declared potency on the label of the USP Reference Standard.

Assay Preparation: For compositions having about the same amylase activity as the USP Pancreatin Amylase and Protease Reference Standard, weigh accurately about 40 mg of Pancreatin into a suitable mortar. (For compositions having a different amylase activity, weigh accurately the amount necessary to obtain an Assay Preparation having amylase activity per mL corresponding approximately to that of the Standard Preparation.) Add about 3 mL of pH 6.8 phosphate buffer, and triturate for 5 to 10 minutes. Transfer the mixture with the aid of pH 6.8 phosphate buffer to a 100-mL volumetric flask, dilute with pH 6.8 phosphate buffer to volume, and mix.

Procedure: Prepare four stoppered, 250-mL conical flasks, and mark them S, U, BS, and BU. Pipet into each flask 25 mL of Substrate Solution, 10 mL of pH 6.8 phosphate buffer, and 1 mL of sodium chloride solution (11.7 in 1000), insert the stoppers, and mix. Place the flasks in a water bath maintained at 25±0.1° C., and allow them to equilibrate. To flasks BU and BS add 2 mL of 1 N hydrochloric acid, mix, and return the flasks to the water bath. To flasks U and BU add 1.0-mL portions of the Assay Preparation, and to flasks S and BS add 1.0 mL of the Standard Preparation. Mix each, and return the flasks to the water bath. After 10 minutes, accurately timed from the addition of the enzyme, add 2-mL portions of 1 N hydrochloric acid to flasks S and U, and mix. To each flask, with continuous stirring, add 10.0 mL of 0.1 N iodine VS, and immediately add 45 mL of 0.1 N sodium hydroxide. Place the flasks in the dark at a temperature between 15° C. and 25° C. for 15 minutes. To each flask add 4 mL of 2 N sulfuric acid, and titrate with 0.1 N sodium thiosulfate VS to the disappearance of the blue color. Calculate the amylase activity, in USP Units per mg, of the composition taken by the formula:

$$100(C_S/W_U)(V_{BU}-V_U)/(V_{BS}-V_S),$$

in which $C_S$ is the amylase activity of the Standard Preparation, in USP Units per mL, $W_U$ is the amount, in mg, of composition taken, and $V_U$, $V_S$, $V_{BU}$, and $V_{BS}$ are the volumes, in mL, of 0.1 N sodium thiosulfate consumed in the titration of the solutions in flasks U, S, BU, and BS, respectively.

Example 4. Dry Powder Composition

Dry powder ingredients of the invention were mixed together in the amounts shown in Table 1 with standard mixing equipment.

TABLE 1

| Ingredient | Amount |
| --- | --- |
| Protease | 388,000 USP Units (10 mg) |
| Lipase | 71,400 USP Units (57 mg) |
| Amylase | 460,000 USP Units (588 mg) |
| L-Arginine | 50 mg |
| Lactoferrin | 50 mg |
| Vitamin B12 | 0.25 mg |
| Inert Carrier Base | 244.75 mg |
| Total | 1000 mg |

The protease used was the Neutral Protease derived from *Bacillus subtilis* obtainable commercially from Bio-Cat (Troy, VA). The Neutral Protease is mainly an endoprotease that tends to cleave peptide bonds at random within the protein structure. The Neutral Protease is supplied as a white to tan powder that is readily soluble in water. The Neutral Protease is active in a pH range of 5.5-9.0, with an optimum at pH 7.0. The Neutral Protease is active in a temperature range of 30° C. to 70° C., with an optimum at 55° C. The Neutral Protease is stabilized with calcium salts and sodium chloride. The Neutral Protease contains protease in an amount of 40-53% w/w, tapioca dextrin an amount of 26-36% w/w, and maltodextrin (waxy maize) as the remainder. The Neutral Protease has a protease activity of 2 million PC/g. The Neutral Protease has protease activity classified by the International Union of Biochemistry (IUB) under number 3.4.24.28 and a CAS number of 9001-92-7.

The lipase used was the Fungal Lipase derived from *Rhizopus oryzae* obtainable commercially from Bio-Cat (Troy, VA). The Fungal Lipase is non-specific and hydrolyzes short, medium, and long chain fatty acids at the 1, 2, or 3 positions of tri-, di-, and monoglycerides. The Fungal Lipase is supplied as a white to tan powder that is soluble in water. The Fungal Lipase is active in a pH range of 4.0-8.0 with an optimum at pH 7.0. The Fungal Lipase is active in a temperature range of 25° C. to 45° C. with an optimum around 37° C. The Fungal Lipase contains lipase in an amount of 5-10% w/w, potato dextrin in an amount of 37-51% w/w, and maltodextrin (waxy maize) as the remainder. The Fungal Lipase has a lipase activity of 150,000 FIP/g. The Fungal Lipase has lipase activity classified by the International Union of Biochemistry (IUB) under number 3.1.1.3 and a CAS number of 9001-62-1.

The amylase used was the Bacterial Amylase derived from *Bacillus amyloliquefaciens* obtainable commercially from Bio-Cat (Troy, VA). The Bacterial Amylase randomly hydrolyzes the α-D-1→4 glycosidic bonds in starch to produce soluble dextrins and low levels of glucose. The Bacterial Amylase is supplied as a white to tan powder that is readily soluble in water. The Bacterial Amylase is active in a pH range of 4.0-8.5 with an optimum at pH 5.5. The Bacterial Amylase is active in a temperature range of 25° C. to 80° C. with an optimum at 70° C. The Bacterial Amylase is stabilized in the presence of starch, calcium ions, and sodium ions. The Bacterial Amylase contains lipase in an amount of 27-37% w/w, potato starch in an amount of 20-29% w/w, and maltodextrin (waxy maize) as the remainder. The Bacterial Amylase has amylase activity of 300,000 BAU/g. The Bacterial Amylase has amylase activity classified by the International Union of Biochemistry (IUB) under number 3.2.1.1 and a CAS number of 9000-90-2.

The L-arginine used was L-arginine monohydrochloride from Centian (Ningbo, China). The L-arginine was provided as white colorless crystals.

The lactoferrin used was Prodiet Lactoferrin from Ingredia (Arras, France). The Prodiet Lactoferrin contained 97.6% w/w lactoferrin protein and 13.0 mg/100 g iron.

The vitamin B12 was Vitamin B12 Additive from NCPC Hebei Lexin Pharmaceutical Co., Ltd. (Hebei, China). The Vitamin B12 Additive contained 1% w/w vitamin B12 in starch.

The inert carrier base was a mixture of lactose powder and poultry liver powder. The lactose powder was Foremost Fast Flo® Lactose from Foremost Farms (code no. ORM-1991) (Rothschild, WI). The Foremost Fast Flo® Lactose was provided as a white crystalline powder, spray-dried mixture of crystalline and amorphous lactose. The poultry liver powder was Spray Dried Chicken Liver from Van Elderen Inc. (product no. 201) (Shelbyville, MI). The Spray Dried Chicken Liver contained 61.11% w/w protein, 24.14% w/w fat, 4.40% w/w moisture, and 4.00% w/w ash.

The mixture was placed into containers and subsequently aliquoted onto feed at 1 teaspoon per meal. The powder of the invention was added to moistened dog food (canned or dry). Thorough mixing was employed to bring the enzymes into close contact with the food particles. Incubation at room temperature for 15-20 minutes before feeding appeared to enhance the digestive process. A dog with EPI consumed the meal.

Example 5. Mixing Dry Powder Composition in Liquid

The ingredients of Table 1 were mixed together into a powder using standard mixing equipment. The powder was then mixed with vegetable oil at a rate of 1 gram per ml of oil to create a slurry. The slurry was sprayed onto extruded dog food (kibble) as the extruded food exited the extruder. The invention was coated onto the surface of the kibble and given to a dog to consume.

Example 6. Amylase Enzyme Analysis

Amylase enzyme from porcine and *Bacillus amyloliquefaciens* at 1 mg/ml concentration and a control of no enzymes were subjected to the Benedict's Test for 10 minutes at pH 7, 38° C., followed by spectrophotometric analysis at 580 nM. The absorbance results are shown in Table 2.

TABLE 2

| Enzyme | Substrate | Control | Porcine | Microbial | N |
|---|---|---|---|---|---|
| Amylase | Starch | 0 | 2.087 +/− 0.11 | 3.71 +/− 0.12 | n = 4 |
| Amylase | Maltose | 0 | 3.108 +/− 0.15 | 5.69 +/− 0.21 | n = 4 |
| Amylase | Dextrose | 0 | 3.078 +/− 0.13 | 5.6 +/− 0.25 | n = 4 |

The results indicated that amylase from the microbial source gave a higher absorbance value than from the porcine source for the substrates tested. This unexpected result indicates a superior efficacy of microbial amylase compared to porcine amylase.

Example 7. Protease Enzyme Analysis

Protease enzyme from porcine and *Bacillus subtilis* at 1 mg/ml concentration and a control of no enzymes were subjected the Biuret Test, followed by spectrophotometric analysis at 630 nM. The results are shown in Table 3.

TABLE 3

| Enzyme | Substrate | Control | Porcine | Microbial | N |
|---|---|---|---|---|---|
| Protease | BSA | 0 | 3.27 +/− 0.12 | 4.21 +/− 0.13 | n = 4 |

The results indicated that proteases from the microbial source gave a higher absorbance value than from the porcine source for the substrates tested. This unexpected result indicates a superior efficacy of microbial proteases compared to porcine proteases.

Example 8. Lipase Enzyme Analysis

Lipase enzyme from porcine and *Rhizopus oryzae* at 1 mg/ml concentration and a control of no enzymes were subjected the free fatty acid (Phenolphthalein) Test followed by spectrophotometric analysis at 480 nM. The results are in Table 4.

TABLE 4

| Enzymes | Substrate | Control | Porcine | Microbial | N |
|---|---|---|---|---|---|
| Lipase | Fat Vegetable oil | 0 | 3.17 +/− 0.11 | 4.72 +/− 0.12 | n = 4 |

The results indicated that lipases from the microbial source gave a higher absorbance value than from the porcine source for the substrates tested. This unexpected result indicates a superior efficacy of microbial lipases compared to porcine lipases.

Example 9. Efficacy Trial—Blood Markers

An efficacy trial with dogs with clinically diagnosed EPI were treated with the invention as formulated in Example 4. These dogs exhibited EPI symptoms including loose feces, poor skin conditions, poor appetite and poor body weight. Prior to treatment, the dogs (N=3) had blood drawn to examine cobalamin levels, canine trypsin like immunoreactivity (cTLI), folate levels, and the bacterial dysbiosys index using standard analytical methods. The animals were then given twice daily doses of an exemplary composition of the invention in their feed as described in Example 1 for a duration of 1 to 3 months. Additional blood was drawn and measured again for cobalamin levels, canine trypsin like immunoreactivity, folate levels, and the bacterial dysbiosys index.

The results are shown in Table 5 below for comparison between the pre- and post-treatment parameters.

TABLE 5

EPI parameters in dogs treated with the composition of Example 4.

| | Pre-treatment | Post-treatment | Ref interval |
|---|---|---|---|
| Cobalamin (Fasting: ng/L) | 150 ± 20 | 360 ± 20 | 251-908 |
| Folate (Fasting, µg/L) | 5.2 ± 0.5 | 15.9 ± 1 | 7.7-24.4 |
| cTLI (Fasting, µg/L) | 50 ± 1 | 15 ± 1 | 5.7-45.2 |
| Dysbiosis index | 1.3 ± 0.2 | −1 ± 0.1 | <0 |

The results show that the animals were all outside the normal reference range prior to treatment. An elevated pretreatment cTLI level is consistent with these dogs having chronic pancreatitis as well. Decreased cobalamin and folate pretreatment levels are indicative of the dogs having EPI. The pretreatment dysbiosis index is indicative that the dogs had a microbial imbalance in the gut that is associated with the diarrhea. However, after the exemplary composition of the invention was included in the dogs' diet statistical improvement (p>0.05 in all cases) occurred in all the parameters measured. It was unexpected and a surprise that the cTLI index dropped into the normal range. These results are consistent with the concept that the compositions of the invention can also be used to treat pancreatitis in addition to EPI. As the animals consumed the exemplary composition of the invention in their diet, positive changes occurred in the blood parameters and the microbial dysbiosis index also improved along with the consistency of the feces from loose form to a solid form. These improvements are consistent with improved overall health of the animals and the resolution of the symptoms of EPI. These results show that the compositions of the invention are effective for use in dogs with EPI and pancreatitis.

Example 10. Efficacy Trial—Weight Gain

Dogs diagnosed with EPI that were exhibiting weight loss and having poor appetite and poor skin condition were selected for treatment with the exemplary composition of the invention as described in Example 4. These dogs were given doses twice daily as in Table 4 for one month and measured for weight gain. Dramatic weight gain was observed in some dogs in that initial period. Dogs that did not improve as dramatically were then treated up to 3 months to improve gain. The results are seen in Table 6 for weight gain in dogs with EPI treated with the composition.

TABLE 6

Weight gain in EPI dogs treated with a composition of the invention.

| | Dog 1 | Dog 2* | Dog 3 | Dog 4* |
|---|---|---|---|---|
| Before Treatment Weight (lbs) | 30 | 54.5 | 51 | 65.2 |
| After Treatment Weight (lbs) | 34 | 59 | 57 | 70.6 |
| Body Weight % Increase using composition of invention | 13 | 8 | 11 | 8 |

*Treatment for 3 months

The results indicate that use of the compositions of the invention is effective for reversing weight loss in dogs that have weight loss due to EPI. These dogs regain their appetite when the invention was included in their daily diet. By using the invention, dogs can increase their weight from 8-13% and regain their normal weight status. In addition, the skin condition of these animals improved when the invention was included in their diet. These results are consistent with the invention being an efficacious treatment for EPI.

The amounts of each of the components in the composition may be varied from the amounts described herein depending upon the nature of the delivery drug, the weight and condition of the animal to be treated, and the unit dosage desired. Those of ordinary skill in the art will be able to adjust dosage amounts as required.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

REFERENCES

Buccigrossi V, de Marco G et al. Lactoferrin induces concentration-dependent functional modulation of intestinal proliferation and differentiation, Pediatr Res. 2007 April; 61(4):410-4.

Bruni N., Teresa M., Capucchio et al. Antimicrobial Activity of Lactoferrin-Related Peptides and Applications in Human and Veterinary Medicine Molecules 2016, 21(6), 752.

Leocádio P C, Antunes M M, Teixeira L G, Leonel A J, Alvarez-Leite J I, Machado D C, 20 Generoso S V, Cardoso V N, Correia M I. L-arginine pretreatment reduces intestinal mucositis as induced by 5-F U in mice. Nutr Cancer. 2015; 67(3):486-93.

Soetart N, Rochel D, Drut A, Jaillardon L. Serum cobalamin and folate as prognostic factors in canine exocrine pancreatic insufficiency: An observational cohort study of 299 dogs. Vet J. 2019 January; 243:15-20.

Talukder M J, Harada E. Bovine lactoferrin protects lipopolysaccharide-induced diarrhea modulating nitric oxide and prostaglandin E2 in mice. Can J Physiol Pharmacol. 2007 February; 85(2):2008.

Umathea, S N, N. I. Kochara, N. S. Jainb, P. V. Dixit. Gastrointestinal dysfunction in diabetic rats relates with a decline in tissue 1-arginine content and consequent low levels of nitric oxide. Nitric Oxide Volume 20, Issue 2, 1 Mar. 2009, Pages 129-133.

Velickovic K, Markelic M et al. Long-term dietary L-arginine supplementation increases endothelial nitric oxide synthase and vasoactive intestinal peptide immunoexpression in rat small intestine. Eur J Nutr. 2014 April; 53(3): 813-21.

Wapnir R A, M A Wingertzahn, S Teichberg L-arginine in low concentration improves rat intestinal water and sodium absorption from oral rehydration solutions. Gut 1997; 40: 602-607.

What is claimed is:

1. An oral ingestible composition for treating exocrine pancreatic insufficiency and a secondary gastrointestinal disorder thereof comprising one or more of small intestinal bacterial overgrowth, gastroenteritis, mucositis, intestinal villi degradation, and intestinal mucosa degradation in a mammal, the composition comprising active ingredients in an inert carrier base, wherein the active ingredients comprise:
   a protease, wherein the protease is present in the composition in an amount from 200,000 USP Units/g to 800,000 USP Units/g;
   a lipase, wherein the lipase is present in the composition in an amount from 35,000 USP Units/g to 140,000 USP Units/g;
   an amylase, wherein the amylase is present in the composition in an amount from 230,000 USP Units/g to 920,000 USP Units/g; and
   L-arginine, wherein the L-arginine is present in the composition in an amount effective to treat the secondary gastrointestinal disorder and is present in the composition in an amount from 2.5% w/w to 10% w/w.

2. The composition of claim 1, wherein:
   the protease comprises an enzyme with an International Union of Biochemistry (IUB) classification of 3.4.24.28;
   the lipase comprises an enzyme with an International Union of Biochemistry (IUB) classification of 3.1.1.3; and
   the amylase comprises an enzyme with an International Union of Biochemistry (IUB) classification of 3.2.1.1.

3. The composition of claim 1, wherein the active ingredients further comprise vitamin B12.

4. The composition of claim 3, wherein the vitamin B12 is present in the composition in an amount from 0.01% w/w to 0.05% w/w.

5. The composition of claim 3, wherein the vitamin B12 is present in the composition in an amount effective to treat vitamin B12 deficiency.

6. The composition of claim 1, wherein the active ingredients further comprise a non-heme, iron-binding glycoprotein.

7. The composition of claim 6, wherein the non-heme, iron-binding glycoprotein is selected from the group consisting of ferritin, lactoferrin, transferrin, and ovotransferrin.

8. The composition of claim 6, wherein the non-heme, iron-binding glycoprotein is at least partially present in apo form.

9. The composition of claim 6, wherein non-heme, iron-binding glycoprotein is present in the composition in an amount from 2.5% w/w to 10% w/w.

10. The composition of claim 1, wherein the inert carrier base is present in the composition in an amount from 12.5% w/w to 50% w/w.

11. The composition of claim 1, wherein the oral ingestible composition is in a powder form.

12. The composition of claim 1, wherein:
    the protease:
      is a microbially produced enzyme;
      is a microbial enzyme; and
      comprises an enzyme with an International Union of Biochemistry (IUB) classification of 3.4.24.28;
    the lipase:
      is a microbially produced enzyme;
      is a microbial enzyme; and
      an enzyme with an International Union of Biochemistry (IUB) classification of 3.1.1.3;
    the amylase:
      is a microbially produced enzyme;
      is a microbial enzyme; and
      comprises an enzyme with an International Union of Biochemistry (IUB) classification of 3.2.1.1; and
    the oral ingestible composition is in a powder form.

13. A method for treating exocrine pancreatic insufficiency and a secondary gastrointestinal disorder thereof comprising one or more of small intestinal bacterial overgrowth, gastroenteritis, mucositis, intestinal villi degradation, and intestinal mucosa degradation in a mammal, the method comprising administering the composition of claim 1 to the mammal.

14. The method of claim 13, wherein the composition is in a powder form, the composition is added in powder form to or mixed with food prior to the administering to thereby form a composition-supplemented food, and the administering comprises feeding the composition-supplemented food to the mammal.

15. The method of claim 13, wherein the composition is in a powder form, the composition in powder form is mixed with a liquid to thereby form a composition-supplemented liquid, the composition-supplemented liquid is added to or mixed with food prior to the administering to thereby form a composition-supplemented food, and the administering comprises feeding the composition-supplemented food to the mammal.

16. The method of claim 13, wherein the composition is administered to the mammal in an amount and for a time effective to elicit at least one of the following effects:
    a normalization of fasting blood cobalamin levels;
    a normalization of fasting blood folate levels;
    a normalization of fasting blood trypsin-like immunoreactivity levels;
    a normalization of dysbiosis index; and
    an increase in weight.

* * * * *